(12) United States Patent
Weiner

(10) Patent No.: US 7,020,517 B2
(45) Date of Patent: Mar. 28, 2006

(54) FIBRILLATION/TACHYCARDIA MONITORING AND PREVENTIVE SYSTEM AND METHODOLOGY

(75) Inventor: Michael L. Weiner, Webster, NY (US)

(73) Assignee: Biophan Technologies, Inc., West Henrietta, NY (US)

( * ) Notice: Subject to any disclaimer, the term of this patent is extended or adjusted under 35 U.S.C. 154(b) by 152 days.

(21) Appl. No.: 10/783,735

(22) Filed: Feb. 20, 2004

(65) Prior Publication Data

US 2005/0187582 A1 Aug. 25, 2005

(51) Int. Cl.
*A61N 1/362* (2006.01)

(52) U.S. Cl. .......................................................... 607/4
(58) Field of Classification Search ............... 607/4–28
See application file for complete search history.

(56) References Cited

U.S. PATENT DOCUMENTS

| | | | |
|---|---|---|---|
| 5,447,520 A * | 9/1995 | Spano et al. .................... | 607/5 |
| 5,782,873 A | 7/1998 | Collins | |
| 6,032,074 A | 2/2000 | Collins | |
| 6,256,537 B1 * | 7/2001 | Stoop et al. .................... | 607/14 |
| 2002/0143266 A1 | 10/2002 | Bock | |
| 2003/0144572 A1 | 7/2003 | Oschman et al. | |
| 2004/0215261 A1 | 10/2004 | Begemann et al. | |

OTHER PUBLICATIONS

William Ditto; Mark Spano, "Self-organized biological dynamics & nonlinear control : toward understanding complexity, chaos, and emergent function in living systems /Cambridge, UK ;," edited by Jan Walleczek , New York : Cambridge University Press, 2000, Chapter 15, pp. 341-373 "Electromagnetic . . . ".

(Continued)

*Primary Examiner*—Scott M. Getzow
(74) *Attorney, Agent, or Firm*—Basch & Nickerson LLP:; Michael J. Nickerson

(57) ABSTRACT

A cardiac assist device senses conditions of a heart and controls the generation of various electrical stimuli in response to sense conditions of the heart. The cardiac assist device generates a electrical pulse so as to defibrillate a fibrillated heart when the cardiac assist device determines from the sensed conditions a state of fibrillation. The cardiac assist device generates a chaos control electrical signal so as to bring a pre-fibrillated heart condition back into a normal beating condition when the cardiac assist device determines from the sensed conditions a pre-state of fibrillation. Lastly, the cardiac assist device generates an electrical enhancement signal that causes a threshold of pacing cells in the heart to be exceeded in response to a subthreshold stimulus when the cardiac assist device determines from the sensed conditions a subthreshold pacing signal.

31 Claims, 5 Drawing Sheets

OTHER PUBLICATIONS

William Ditto; Mark Spano, "Self-organized biological dynamics & nonlinear control : toward understanding complexity, chaos, and emergent function in living systems /Cambridge, UK ;," edited by Jan Walleczek , New York : Cambridge University Press, 2000.

FX Witkowski; KM Kavanagh; PA Penkoske; R Plonsey; ML Spano; WK Ditto; DT Kaplan, "Evidence for Determinism in Ventricular Fillibration," Physical Review Letters, The American Physical Society, vol. 75 (No. 6), p. 1230-1233, ( Feb. 18, 1995).

Daniel T. Kaplan, "Finding and Characterizing Unstable Fixed Points By Controlling System Dynamics," World Scientific, Submitted on Sep. 30, 1999, p. 1-11.

Dana Mckenzie, "Making Sense of a Heart Gone Wild," SCIENCE, www.sciencemag.org, p. 786 , ( Feb. 6, 2004).

S Alsonso; F Sagues; A S Mikhailov, "Taming Winfree Turbulence of Scroll Waves in Excitable Media," Science Magazine, www.sciencxpress.org; Sciencexpress, ( Jan. 30, 2003).

* cited by examiner

FIBRILLATION/TACHYCARDIA MONITORING AND PREVENTIVE SYSTEM AND METHODOLOGY

CROSS REFERENCE TO RELATED PATENT APPLICATIONS

The subject matter of co-pending U.S. patent application Ser. No. 09/885,867, filed on Jun. 20, 2001, entitled "Controllable, Wearable MRI-Compatible Cardiac Pacemaker With Pulse Carrying Photonic Catheter And VOO Functionality"; co-pending U.S. patent application Ser. No. 09/885,868, filed on Jun. 20, 2001, entitled "Controllable, Wearable MRI-Compatible Cardiac Pacemaker With Power Carrying Photonic Catheter And VOO Functionality"; co-pending U.S. patent application Ser. No. 10/037,513, filed on Jan. 4, 2002, entitled "Optical Pulse Generator For Battery Powered Photonic Pacemakers And Other Light Driven Medical Stimulation Equipment"; co-pending U.S. patent application Ser. No. 10/037,720, filed on Jan. 4, 2002, entitled "Opto-Electric Coupling Device For Photonic Pacemakers And Other Opto-Electric Medical Stimulation Equipment"; co-pending U.S. patent application Ser. No. 09/943,216, filed on Aug. 30, 2001, entitled "Pulse Width Cardiac Pacing Apparatus"; co-pending U.S. patent application Ser. No. 09/964,095, filed on Sep. 26, 2001, entitled "Process for Converting Light"; co-pending U.S. patent application Ser. No. 09/921,066, filed on Aug. 2, 2001, entitled "MRI-Resistant Implantable Device"; co-pending U.S. patent application Ser. No. 10/077,842, filed on Feb. 19, 2002, entitled "An Electromagnetic Interference Immune Tissue Invasive System"; co-pending U.S. patent application Ser. No. 10/077,823, filed on Feb. 19, 2002, entitled "An Electromagnetic Interference Immune Tissue Invasive System"; co-pending U.S. patent application Ser. No. 10/077,887, filed on Feb. 19, 2002, entitled "An Electromagnetic Interference Immune Tissue Invasive System"; co-pending U.S. patent application Ser. No. 10/077,883, filed on Feb. 19, 2002, entitled "An Electromagnetic Interference Immune Tissue Invasive System"; and co-pending U.S. patent application Ser. No. 10/077,958, filed on Feb. 19, 2002, entitled "An Electromagnetic Interference Immune Tissue Invasive System".

The entire content of each of the above noted co-pending U.S. patent application Ser. No. 09/885,867; 09/885,868; 10/037,513; 10/037,720; 09/943,216; 09/964,095; 09/921,066; 10/077,842; 10/077,823; 10/077,887; 10/077,883; and 10/077,958 is hereby incorporated by reference.

FIELD OF THE PRESENT INVENTION

The present invention relates generally to an implantable device that is capable of monitoring cardiac conditions and preventing tachycarddia. More particularly, the present invention is directed to an implantable system that monitors cardiac electrical to determined a covergence upon uniformity and applies electrical noise into the cardiac evironment to break-up the convergence upon uniformity.

BACKGROUND OF THE PRESENT INVENTION

The heart is a series of pumps that are carefully controlled by a very special electrical system. This electrical system attempts to regulate the heart rate between 60 and 150 beats per minute. With normal conduction, the cardiac contractions are very organized and timed so that the top chambers (the atria) contract before the lower chambers and the heart rate is maintained between 60 and 150 beats per minute.

Abnormally fast heart rates, called tachycardias, occur when the ventricular chambers beat too quickly. In such an instance, the ventricles may not be able to fill with enough blood to supply the body with the oxygen rich blood that it needs. Conventionally, ventricular tachycardia ("VT") has been controlled by medication and electrical methods. The most common conventional electrical therapy for VT is implantation of a device known as an Implantable Cardioverter Defibrillator or ICD.

The conventional ICD applies an electric shock to the heart muscle to interrupt or disrupt the fast rhythm. The electric shock may be in the form of specially timed pacemaker pulses (unfelt by the patient), called antitachycardia pacing, and/or by high voltage shock. The high voltage shock, if required, is usually felt by the patient.

Cardiac pacers, which provide stimulation to a patient's heart, by means of amplitude and frequency modulated electrical pulses, have been developed for permanent or temporary applications. The two most common types of cardiac pacers currently in use are pacemakers and implantable cardioverter-defibrillators (ICD). Cardiac pacers can be implanted in a suitable location inside the patient's body or located outside the patient's body.

The human heart may suffer from two classes of rhythmic disorders or arrhythmias: bradycardia and tachyarrhythmia. Bradycardia occurs when the heart beats too slowly, and may be treated by a common implantable pacemaker delivering low voltage (about 3 V) pacing pulses.

The conventional implantable pacemaker is usually contained within a hermetically sealed enclosure, in order to protect the operational components of the device from the harsh environment of the body, as well as to protect the body from the device. This implantable pacemaker operates in conjunction with one or more electrically conductive leads, adapted to conduct electrical stimulating pulses to sites within the patient's heart, and to communicate sensed signals from those sites back to the implanted device.

Furthermore, the conventional implantable pacemaker typically has a metal case and a connector block mounted to the metal case that includes receptacles for leads which may be used for electrical stimulation or which may be used for sensing of physiological signals. The battery and the circuitry associated with the common implantable pacemaker are hermetically sealed within the case. Electrical interfaces are employed to connect the leads outside the metal case with the medical device circuitry and the battery inside the metal case.

Electrical interfaces serve the purpose of providing an electrical circuit path extending from the interior of a hermetically sealed metal case to an external point outside the case while maintaining the hermetic seal of the case. A conductive path is provided through the interface by a conductive pin that is electrically insulated from the case itself.

Such interfaces typically include a ferrule that permits attachment of the interface to the case, the conductive pin, and a hermetic glass or ceramic seal that supports the pin within the ferrule and isolates the pin from the metal case.

In all of the conventional electrical stimulus devices, the conventional ICD senses a fibrillation or tachycardia cardiac state and proceeds to use various measures to bring the heart out of the fibrillation or tachycardia, through defibrillation by antitachycardia pacing, and/or by high voltage shock. In other words, the heart has already reached a dangerous state before the conventional ICDs provide any stimulus to rectify the problem.

Therefore, it is desirable to have a device that can sense or detect an approaching fibrillation or tachycardia cardiac state and take remedial actions prior to the heart entering a dangerous state. Moreover, it is desirable to have a device that can sense or detect a failure of remedial actions and provide, as a backup remedy, the conventional defibrillation by antitachycardia pacing, and/or by high voltage shock.

SUMMARY OF THE PRESENT INVENTION

A first aspect of the present invention is a cardiac assist device. The cardiac assist device includes a primary device housing; a sensor to sense conditions of a heart; and a lead system to transmit and receive signals between the heart and the primary housing. The primary device housing includes a control circuit, in operative communication with the sensor, to control generation of various electrical stimuli in response to sense conditions of the heart; a chaos control generator to generate an electrical signal so as to bring a pre-fibrillated heart condition back into a normal beating condition when the control circuit determines from the sensed conditions a pre-state of fibrillation; and a pacing environment enhancement generator to generating an electrical enhancement signal that causes a threshold of pacing cells in the heart to be exceeded in response to a subthreshold stimulus when control circuit determines from the sensed conditions a subthreshold pacing signal.

A second aspect of the present invention is a method for assisting a heart beat normally. The method senses conditions of a heart; determines a state of the heart from the sensed conditions; generates a control electrical signal so as to bring a pre-fibrillated heart condition back into a normal beating condition when the determined state of the heart is a pre-state of fibrillation, and generates an electrical enhancement signal that causes a threshold of pacing cells in the heart to be exceeded in response to a subthreshold stimulus when the determined state of the heart is a state associated with a subthreshold pacing signal.

BRIEF DESCRIPTION OF THE DRAWINGS

The present invention may take form in various components and arrangements of components, and in various steps and arrangements of steps. The drawings are only for purposes of illustrating a preferred embodiment and are not to be construed as limiting the present invention, wherein.

DETAILED DESCRIPTION OF THE PRESENT INVENTION

Figure 1:
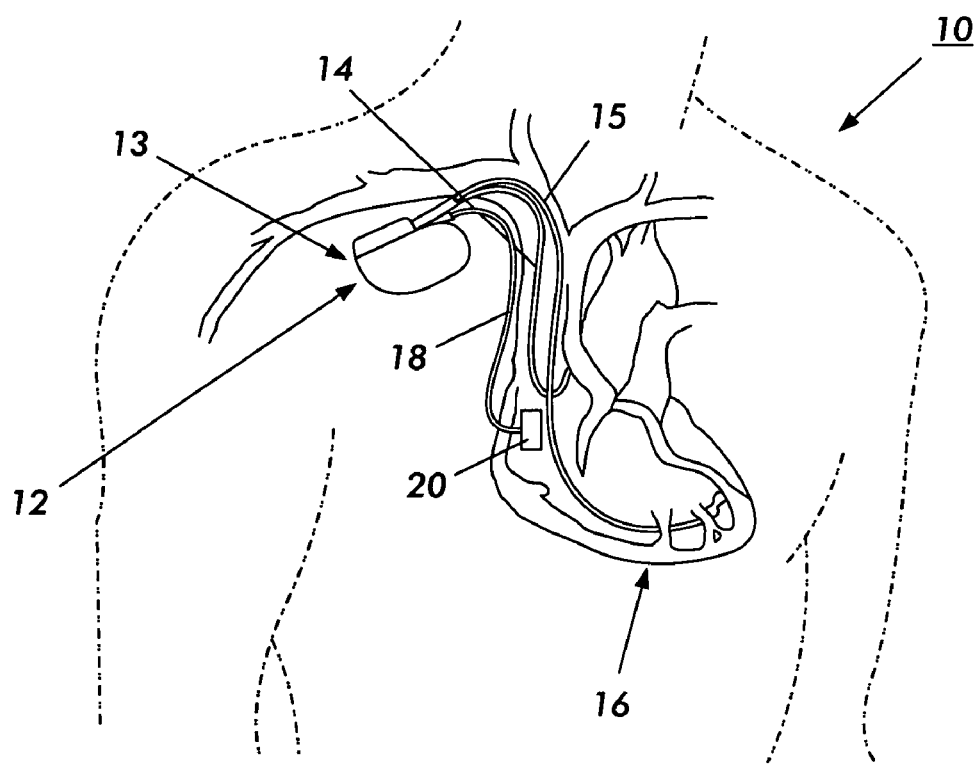
FIG. 1 illustrates one embodiment of a cardiac assist system according to the concepts of the present invention.

The present invention will be described in connection with preferred embodiments; however, it will be understood that there is no intent to limit the present invention to the embodiments described herein. On the contrary, the intent is to cover all alternatives, modifications, and equivalents as may be included within the spirit and scope of the present invention as defined by the appended claims.

For a general understanding of the present invention, reference is made to the drawings. In the drawings, like reference have been used throughout to designate identical or equivalent elements. It is also noted that the various drawings illustrating the present invention are not drawn to scale and that certain regions have been purposely drawn disproportionately so that the features and concepts of the present invention could be properly illustrated.

Current medical research has demonstrated that fibrillation has three detectable stages wherein some intervention is needed by the second stage to prevent fibrillation or actual intervention at the third stage to cause defibrillation. Moreover, from this research, it appears that fibrillation is not necessarily an immediate situation, but fibrillation is a breaking down, over a period of time, of a stable cardiac system into a chaotic cardiac system to finally a pseudo-random cardiac system and heart failure.

Of the stages discussed above, the first stage is a warning stage wherein warning signs are produced indicating that the heart beating may be progressing towards the realization of fibrillation; the second stage is the onset of fibrillation, thus intervention is critical to avoid heart failure and the need for a defibrillation stimulus to bring the heart back into proper rhythm. It is these first two stages that the present invention provides a non-defibrillation stimulus to bring the heart back into proper rhythm. Moreover, the present invention proposes a pre-warning stage wherein a sub-threshold stimulus is provided as a preventive means to avoid the heart from entering the first warning stage of fibrillation.

As illustrated in FIG. 1, a medical device 12 is provided to monitor the conditions of the heart and to provide proper stimulus as dictated by the monitored conditions. Although this embodiment of FIG. 1 illustrates the medical device 12 as implantable, the medical device 12 may be implantable or non-implantable.

Stimulus leads 14 and 15 are connected to the medical device 12 in connector block region 13 using an interface. It is noted that stimulus leads 14 and 15 may be a fiber optic based communication system wherein the fiber optic communication system contains at least one channel within a multi-fiber optic bundle. The fiber optic based communication system is covered with a biocompatible material wherein the biocompatible material is a non-permeable diffusion resistant biocompatible material.

The stimulus leads 14 and 15 may also be a plurality of electrical leads that have a shield therearound to prevent the electrical leads from conducting stray electromagnetic interference. This shield may be a metallic sheath, a carbon composite sheath, or a polymer composite sheath to prevent the electrical leads from conducting stray electromagnetic interference. In addition to the shield or in lieu of the shield, each electrical lead may include an electrical filter wherein the electrical filter removes stray electromagnetic interference from a signal being received from the electrical lead. The electrical filter may comprise capacitive and inductive filter elements adapted to filter out predetermined frequencies of electromagnetic interference. The shield is covered with a biocompatible material wherein the biocompatible material is a non-permeable diffusion resistant biocompatible material.

The stimulus leads 14 and 15 may be unipolar leads, bipolar leads, or a combination of unipolar and bipolar leads.

The stimulus leads 14 and 15 may also be a combination of a fiber optic based communication system and electrical leads. Moreover, the stimulus leads 14 and 15 may be defibrillator leads.

The stimulus leads 14 and 15 may also include a detection circuit (not shown) to detect a phase timing of an external electromagnetic field such that a control circuit alters its operations to avoid interfering with the detected external electromagnetic field.

As further illustrated in FIG. 1, a cardiac sensor lead 18 with associated sensor 20 is connected to the implantable medical device 12 in connector block region 13 using an interface. As discussed above, the present invention provides a means for sensing the cardiac conditions and also provides a means for generating stimuli in response thereto.

With respect to monitoring the cardiac conditions, one embodiment of the present invention contemplates that the sensor 20 is a two-dimensional high-definition (high resolution) touch sensitive patch attached to the heart that provides fast frames of pressure readings from individual pressure sites for the two-dimensional area of interest. In this embodiment, the sensor 20 provides pressure readings from the sensed pressure pulses. These pressure readings are correlated to the pulsing of the heart muscle by a microprocessor located within the implantable medical device 12.

In another embodiment of the present invention, the sensor 20 is a two-dimensional high-definition (high resolution) patch that can measure, capacitively, the voltage. The voltage sensitive sites would be, for example, individual non-destructive floating-gate charge-sensing amplifiers located in very defined areas without affecting the voltage in other areas.

Figure 2:
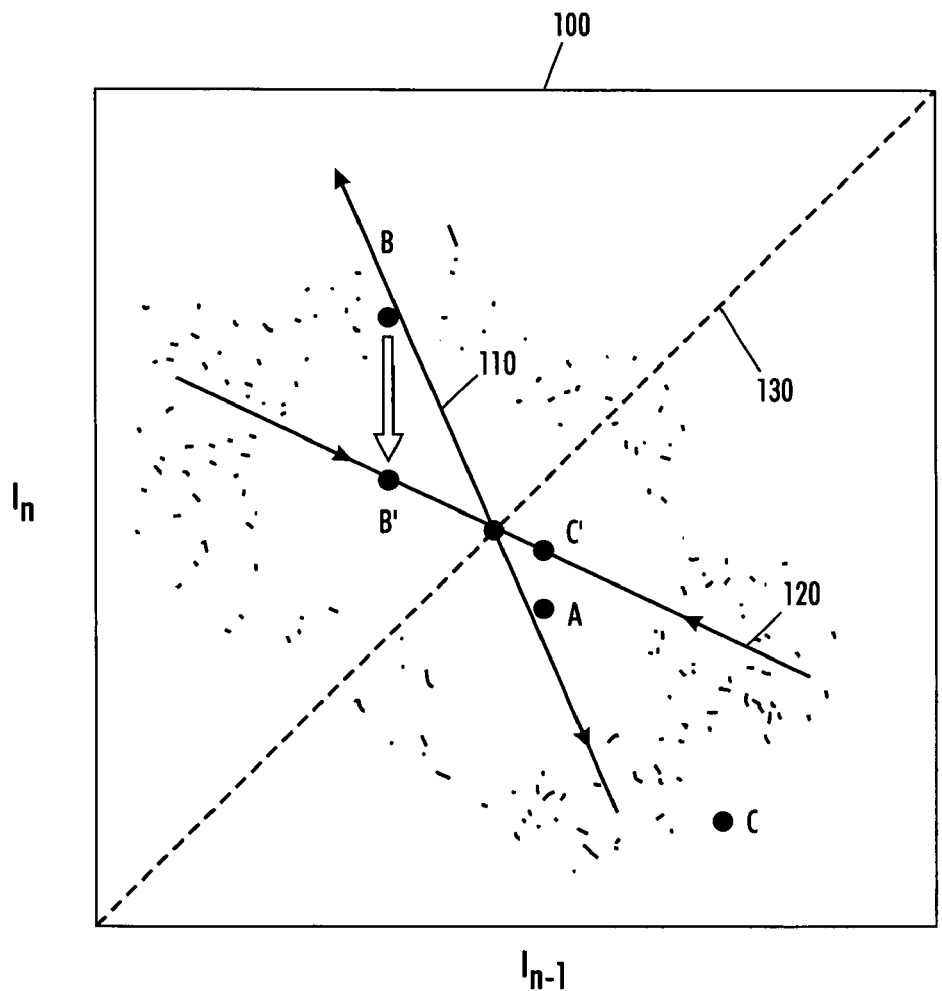
FIG. 2 illustrates an example of a Poincaré map used by the present invention to manage the generation of electrical stimulus during a pre-fibrillation stage.

According to the concepts of the present invention, the information received from the sensor 20 is processed by the microprocessor so as to generate information that is equivalent to a Poincaré map of the sensed situation. Upon this information being internally mapped by the microprocessor, the sequence of the data points is used to determine the stable and unstable directions of the Poincaré map. An example of this determination is illustrated by FIG. 2 wherein the determined stable 120 and unstable 110 directions (manifolds) and the unity line 130 of the Poincaré map 100 are shown.

A normal functioning heart will have its points lying along or in very close proximity to the stable manifold 120. As shown in FIG. 2, point B represent a condition wherein the system is beginning to become unstable and in the case of the present invention, the heart is showing warning signs of fibrillation. Therefore, when a condition represented by point B of FIG. 2 is sensed by the present invention, a signal is generated to bring the point from B to B'. In other words, the signal generated by the present invention provides chaos control by bringing the condition (B), as illustrated by a Poincaré map, to a new condition (B') that lies along or is in very close proximity to the stable manifold 120 of the Poincaré map.

In other words, the present invention provides a stimulus to prevent fibrillation. According to the concepts of the present invention the stimulus can be managed in amplitude, frequency, and timing (modulation) to be effective. Moreover, the stimulus may be either positive (in that it enhances the natural signal being generated by the heart) or negative (in that is blocks, dampens, or diminishes the natural signal being generated by the heart). The stimulus brings the sensed conditions back to a normal state (points on the Poincaré map back to unity). Simply put the control unit of the present invention translates the measured conditions into Poincaré space, find the difference between a stable condition in Poincaré space and the measured condition in Poincaré space, and translate the Poincaré space difference to a voltage, current, power, or drug stimulus space so that effective treatment can be realized.

Thus, instead of powerful electric jolts from defibrillator paddles to restore a normal heartbeat, the present invention provides a more gentle stimulation during an early warning stage of fibrillation so as to prevent the full onslaught of fibrillation so as to avoid unnecessary harm or discomfort to the patient.

Figure 3:
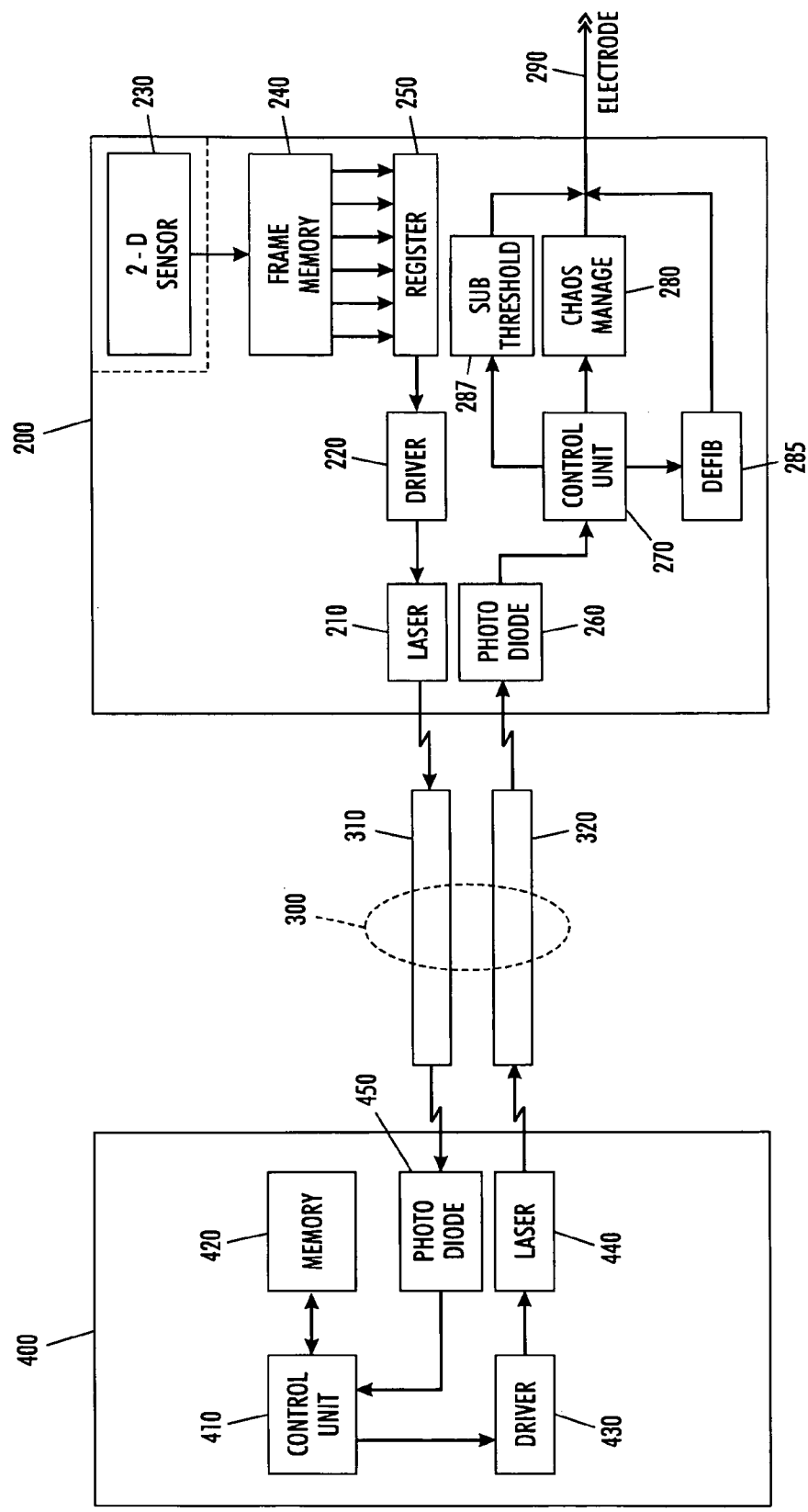
FIGS. 3 and 4 illustrate further embodiments of a cardiac assist system according to the concepts of the present invention.

FIG. 3 illustrates another embodiment of the present invention. As illustrated in FIG. 3, a primary housing 400 includes a control unit 410 that manages the overall operations of the cardiac assist system or device. The control unit 410 is operatively connected to a memory unit 420 that stores the applications needed to control the cardiac assist device as well as the data associated with the sensed conditions of the heart.

For illustrative purposes, the cardiac assist device of FIG. 3 includes a fiber optic communication system comprising an optical bundle 300 having optical fibers 310 and 320; lasers 440 and 210 to provide optical pulses between the primary housing 400 and a secondary housing 200; photodiodes 450 and 260 to convert the optical pulses to electrical data signals; and drivers 210 and 340 to convert electrical signals into control signals that cause the optical pulses to be generated.

It is noted that the fiber optic communication system can be replaced with an electrical system, an acoustic system, or a radio transmission system. In such cases the various components described above would be replaced with their equivalent corresponding components.

It is further noted that the fiber optic communication system contains at least one channel within a multi-fiber optic bundle. The fiber optic based communication system is covered with a biocompatible material wherein the biocompatible material is a non-permeable diffusion resistant biocompatible material.

The communication system may also be a plurality of electrical leads that have a shield therearound to prevent the electrical leads from conducting stray electromagnetic interference. This shield may be a metallic sheath, a carbon composite sheath, or a polymer composite sheath to prevent the electrical leads from conducting stray electromagnetic interference. In addition to the shield or in lieu of the shield, each electrical lead may include an electrical filter wherein the electrical filter removes stray electromagnetic interference from a signal being received from the electrical lead. The electrical filter may comprise capacitive and inductive filter elements adapted to filter out predetermined frequencies of electromagnetic interference. The shield is covered with a biocompatible material wherein the biocompatible material is a non-permeable diffusion resistant biocompatible material.

The communication system may be unipolar leads, bipolar leads, or a combination of unipolar and bipolar leads. The communication system may also be a combination of a fiber optic based communication system and electrical leads.

The communication system may also include a detection circuit (not shown) to detect a phase timing of an external electromagnetic field such that a control circuit alters its operations to avoid interfering with the detected external electromagnetic field.

FIG. 3 further illustrates a secondary housing 200 that includes a control unit 270. The control unit 270 is in operative communication with control unit 410 of the primary housing. It is noted that the cardiac assist device of the present invention may be constructed in a single housing and thus only a single control unit would be needed, as will be described below in more detail with respect to FIG. 4.

The secondary housing 200 further includes a sensor 230 to sense the conditions, of the heart. The sensor 230 may be integral to the secondary housing 200 or operatively connected to the secondary housing through optical or electrical leads, or a combination thereof.

With respect to monitoring the cardiac conditions, one embodiment of the present invention contemplates that the sensor 230 is a two-dimensional high-definition (high resolution) touch sensitive patch attached to the heart that provides fast frames of pressure readings from individual pressure sites for the two-dimensional area of interest. In this embodiment, the sensor 230 provides pressure readings from the sensed pressure pulses. These pressure readings are correlated to the pulsing of the heart muscle by the control unit 410.

In another embodiment of the present invention, the sensor 230 is a two-dimensional high-definition (high resolution) patch that can measure, capacitively, the voltage. The voltage sensitive sites would be, for example, individual non-destructive floating-gate charge-sensing amplifiers located in very defined areas without affecting the voltage in other areas.

In a preferred embodiment of the present invention, the information received from the sensor 230 is processed by the control unit 410 so as to generate information that is equivalent to a Poincaré map of the sensed situation. Upon this information being internally mapped by the control unit 410, the sequence of the data points is used to determine the stable and unstable directions of the Poincaré map. The mapped information is stored in memory 420 for use by the control unit 410. It is noted that various memory management schemes, such as compression techniques, may be used to effectively store the required amount of data necessary for proper analysis by the control unit 410. It is preferred that the mapped information be analyzed in its compressed state to conserve memory space.

If a two-dimensional sensor is utilized, the secondary housing 200 would include a frame memory 240 and a register 250 to convert the two-dimensional array of data into a serial data to be transmitted to the primary housing 400.

The control unit 270 controls the operations of a subthreshold stimulus generator 287, a chaos management generator 280, and a defibrillation pulse generator 285. These various generators are connected to an electrode 290 that is connected to the heart.

When the control unit 410 determines that the natural pacing signal of the heart falls below a threshold to trigger the heart to beat, the control unit 410 generates a signal to control unit 270 instructing the control unit 270 to activate the subthreshold stimulus generator 287. Subthreshold stimulus generator 287 generates a signal that causes a threshold of pacing cells in the heart to be exceeded in response to a subthreshold pacing signal or natural stimulus.

The signal generated by the subthreshold stimulus generator 287 may be a noise signal; a periodic signal; a high frequency deterministic signal; a randomly fluctuating intensity signal; a randomly fluctuating frequency signal; or any combination thereof The signal generated by the subthreshold stimulus generator 287 may also be modulated in response to the sensed subthreshold pacing signal.

When the control unit 410 determines that the state of the heart is entering in a pre-fibrillation stage, the control unit 410 generates a signal to control unit 270 instructing the control unit 270 to activate the chaos management generator 280. Chaos management generator 280 generates a signal that prevents the onslaught of fibrillation. The stimulus can be managed in amplitude, frequency, and timing (modulation) to be effective. Moreover, the stimulus may be either positive (in that it enhances the natural signal being generated by the heart) or negative (in that is blocks, dampens, or diminishes the natural signal being generated by the heart). The stimulus brings the sensed conditions back to a normal state (points on the Poincaré map back to unity).

Lastly, when the control unit 410 determines that the state of the heart is in a fibrillation stage, the control unit 410 generates a signal to control unit 270 instructing the control unit 270 to activate the defibrillation pulse generator 285. Defibrillation pulse generator 285 generates a high voltage pulse to defibrillate the heart.

Figure 4:
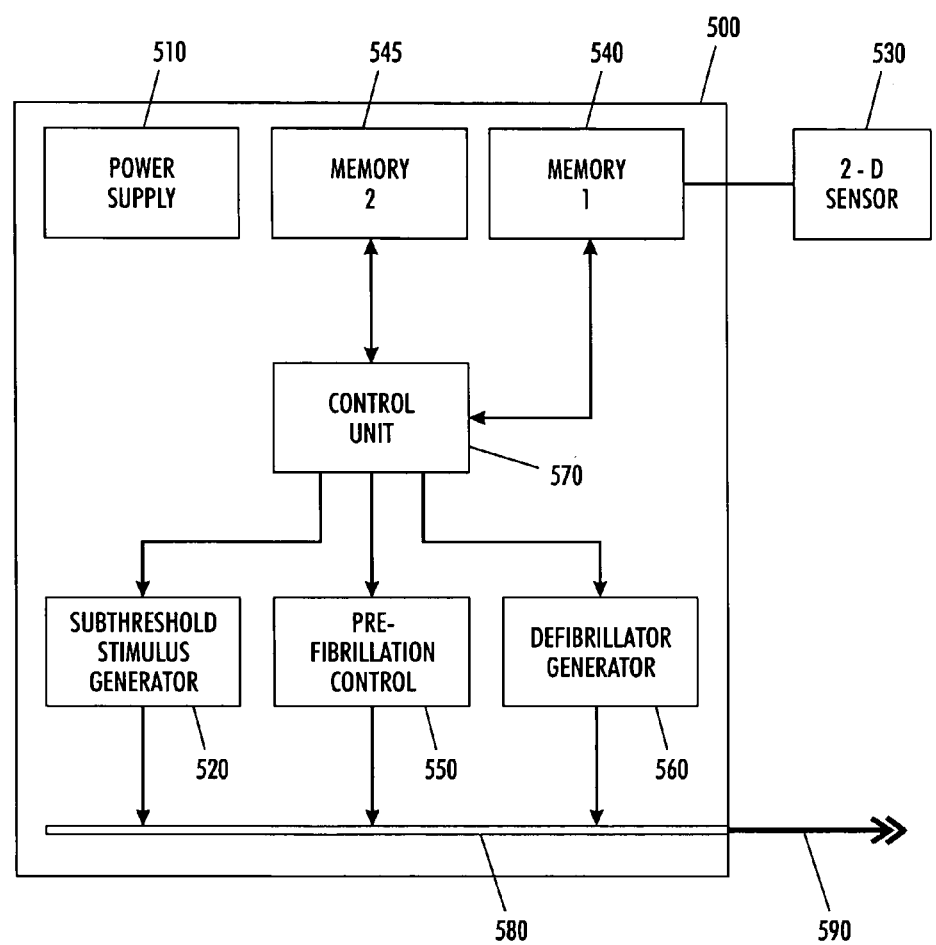

FIG. 4 illustrates another embodiment of the present invention that includes a housing 500 and a control unit 570 therein. The housing 500 is operatively connected to a sensor 530 to sense the conditions of the heart. The sensor 530 may be integral to the housing 500 or operatively connected to the housing through optical or electrical leads, or a combination thereof With respect to monitoring the cardiac conditions, one embodiment of the present invention contemplates that the sensor 530 is a two-dimensional high-definition (high resolution) touch sensitive patch attached to the heart that provides fast frames of pressure readings from individual pressure sites for the two-dimensional area of interest. In this embodiment, the sensor 530 provides pressure readings from the sensed pressure pulses. These pressure readings are correlated to the pulsing of the heart muscle by the control unit 570.

In another embodiment of the present invention, the sensor 530 is a two-dimensional high-definition (high resolution) patch that can measure, capacitively, the voltage. The voltage sensitive sites would be, for example, individual non-destructive floating-gate charge-sensing amplifiers located in very defined areas without affecting the voltage in other areas.

In a preferred embodiment of the present invention, the information received from the sensor 530 is processed by the control unit 570 so as to generate information that is equivalent to a Poincaré map of the sensed situation. Upon this information being internally mapped by the control unit 570, the sequence of the data points is used to determine the stable and unstable directions of the Poincaré map. The mapped information is stored in second memory 545 for use by the control unit 570. It is noted that various memory management schemes, such as compression techniques, may be used to effectively store the required amount of data necessary for proper analysis by the an control unit 570. It is preferred that the mapped information be analyzed in its compressed state to conserve memory space.

If a two-dimensional sensor were utilized, the housing 500 would include a memory 540 to convert the two-dimensional array of data into a serial data to be transmitted to the control unit 570.

The control unit 570 controls the operations of a subthreshold stimulus generator 520, a pre-fibrillation control generator 550, and a defibrillation pulse generator 560. These various generators are connected, via pulse bus 580, to an electrode 590 that is connected to the heart.

When the control unit 570 determines that the natural pacing signal of the heart falls below a threshold to trigger the heart to beat, the control unit 570 generates a signal to activate the subthreshold stimulus generator 520. Subthreshold stimulus generator 520 generates a signal that causes a threshold of pacing cells in the heart to be exceeded in response to a subthreshold pacing signal or natural stimulus.

The signal generated by the subthreshold stimulus generator 520 may be a noise signal; a periodic signal; a high frequency deterministic signal; a randomly fluctuating intensity signal; a randomly fluctuating frequency signal; or any combination thereof The signal generated by the subthreshold stimulus generator 520 may also be modulated in response to the sensed subthreshold pacing signal.

When the control unit 570 determines that the state of the heart is entering in a pre-fibrillation stage, the control unit 570 generates a signal to activate the pre-fibrillation control generator 550. Pre-fibrillation control generator 550 generates a signal that prevents the onslaught of fibrillation. The stimulus can be managed in amplitude, frequency, and timing (modulation) to be effective. Moreover, the stimulus may be either positive (in that it enhances the natural signal being generated by the heart) or negative (in that is blocks, dampens, or diminishes the natural signal being generated by the heart). The stimulus brings the sensed conditions back to a normal state (points on the Poincaré map back to unity).

Lastly, when the control unit 570 determines that the state of the heart is in a fibrillation stage, the control unit 570 generates a signal to activate the defibrillation pulse generator 560. Defibrillation pulse generator 560 generates a high voltage pulse to defibrillate the heart.

Figure 5:
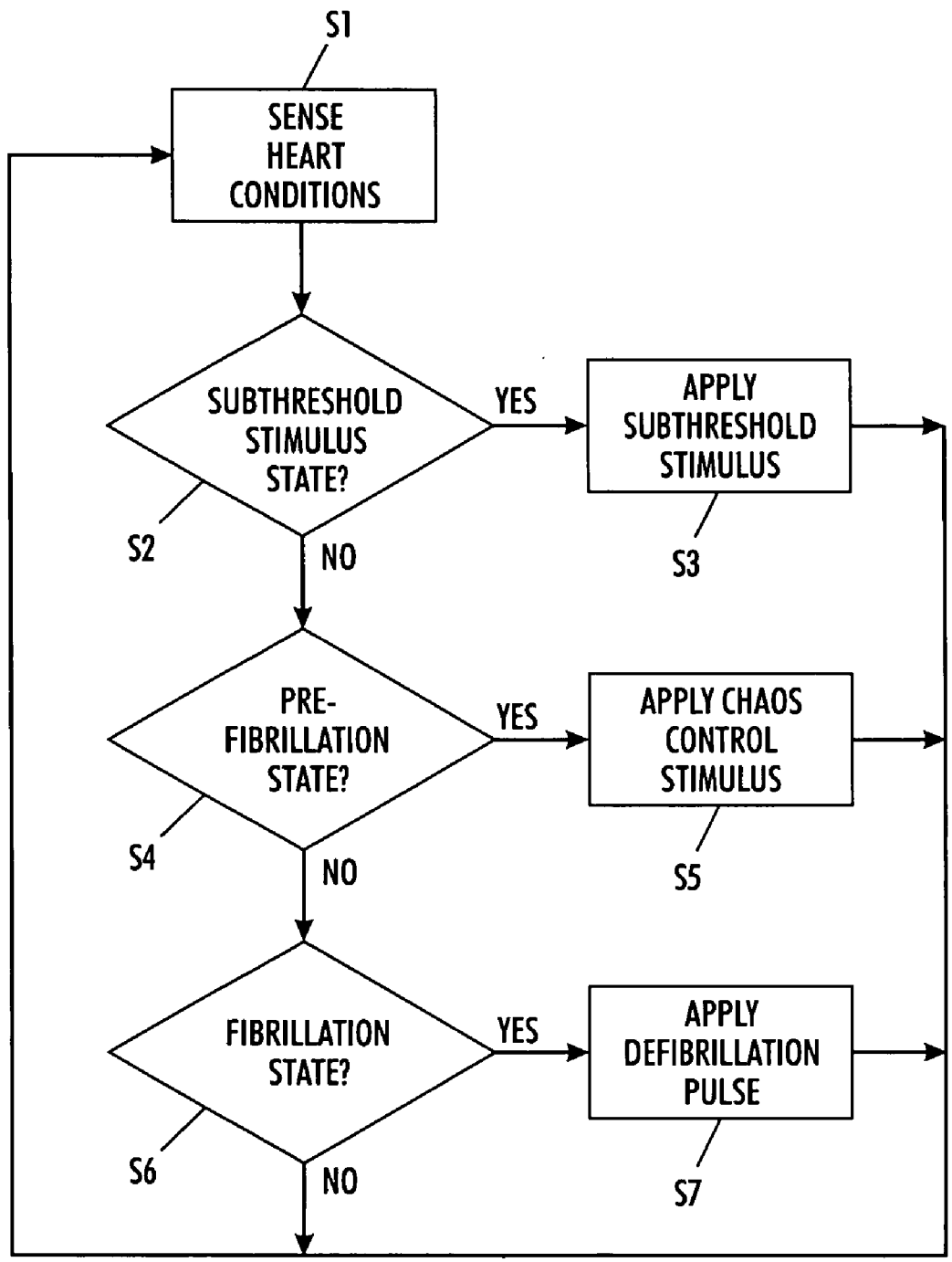
FIG. 5 is a flowchart illustrating the management of a heart according to the concepts of the present invention.

The methodology utilized by the present invention is illustrated in FIG. 5. As illustrated in FIG. 5, step S1 senses the conditions of the heart. If it is determined at step S2 that the natural pacing signal of the heart falls below a threshold to trigger the heart to beat, step S3 causes a signal to be generated that causes a threshold of pacing cells in the heart to be exceeded in response to a subthreshold pacing signal or natural stimulus.

If it is determined at step S4 that the heart is entering in a pre-fibrillation stage, step S5 causes a signal to be generated that prevents the onslaught of fibrillation. If it is determined at step S6 that the heart is entering a fibrillation stage, step S7 causes a high voltage pulse to be generated to defibrillate the heart.

In each of the embodiments described above, the cardiac assist device of the present invention may be contained within a hermetically sealed enclosure, in order to protect the operational components of the device from the harsh environment of the body, as well as to protect the body from the device. The cardiac assist device of the present invention may have a metal case and a connector block mounted to the metal case that includes receptacles for leads which may be used for electrical stimulation or which may be used for sensing of physiological signals. The battery and the circuitry associated with the common implantable pacemaker are hermetically sealed within the case. Electrical interfaces are employed to connect the leads outside the metal case with the medical device circuitry and the battery inside the metal case.

Electrical interfaces serve the purpose of providing an electrical circuit path extending from the interior of a hermetically sealed metal case to an external point outside the case while maintaining the hermetic seal of the case. A conductive path is provided through the interface by a conductive pin that is electrically insulated from the case itself.

Such interfaces typically include a ferrule that permits attachment of the interface to the case, the conductive pin, and a hermetic glass or ceramic seal that supports the pin within the ferrule and isolates the pin from the metal case.

Furthermore, in each of the embodiments described above, the cardiac assist device of the present invention may be constructed to as to be immune or hardened to electromagnetic insult or interference. Although the leads may be fiber optic strands or electrical leads with proper shielding, the actual interface to the tissue, the electrodes, cannot be shielded because the tissue needs to receive the stimulation from the device without interference. This causes the electrodes to be susceptible to electromagnetic interference or insult, and such insult can cause either damage to the tissue area or the circuitry at the other end. To realize immunity from the electromagnetic interference or insult, each electrode has an anti-antenna geometrical shape. The anti-antenna geometrical shape prevents the electrode from picking up and conducting stray electromagnetic interference.

While various examples and embodiments of the present invention have been shown and described, it will be appreciated by those skilled in the art that the spirit and scope of the present invention are not limited to the specific description and drawings herein, but extend to various modifications and changes all as set forth in the following claims.

What is claimed is:

1. A cardiac assist device, comprising:
   a primary device housing;
   a sensor to sense conditions of a heart; and
   a lead system to transmit and receive signals between the heart and said primary housing;
   said primary device housing including,
   a control circuit, in operative communication with said sensor, to control generation of various electrical stimuli in response to sense conditions of the heart,
   a chaos control generator to generate a pre-fibrillation state electrical signal so as to bring a pre-fibrillated heart condition back into a normal beating condition when said control circuit determines from the sensed conditions a pre-state of fibrillation, and
   a pacing environment enhancement generator to generate an electrical enhancement signal, said electrical enhancement signal effectively lowering a threshold for pacing the heart when said control circuit determines from the sensed conditions that a natural pacing signal of the heart has fallen below a threshold to trigger the heart to beat.

2. The cardiac assist device as claimed in claim 1, wherein said electrical enhancement signal comprises a noise signal.

3. The cardiac assist device as claimed in claim 1, wherein said electrical enhancement signal comprises a periodic signal.

4. The cardiac assist device as claimed in claim 1, wherein said electrical enhancement signal comprises a high frequency deterministic signal.

5. The cardiac assist device as claimed in claim 1, wherein said electrical enhancement signal comprises a randomly fluctuating intensity signal.

6. The cardiac assist device as claimed in claim 1, wherein said electrical enhancement signal comprises a randomly fluctuating frequency signal.

7. The cardiac assist device as claimed in claim 1, wherein said electrical enhancement signal is modulated in response to the sensed subthreshold pacing signal.

8. The cardiac assist device as claimed in claim 1, wherein said sensor comprises a two-dimensional high resolution touch sensitive patch attached to the heart to provide fast frames of pressure readings from a two-dimensional array of individual pressure sites.

9. The cardiac assist device as claimed in claim 1, wherein said sensor comprises a two-dimensional high resolution patch to measure, capacitively, a voltage waveform traveling across the heart.

10. The cardiac assist device as claimed in claim 9, wherein said two-dimensional high resolution patch comprises a two-dimensional array of individual non-destructive floating -gate charge-sensing amplifiers.

11. The cardiac assist device as claimed in claim 1, wherein said primary device housing further includes a defibrillation circuit to generate a electrical pulse so as to defibrillate a fibrillated heart when said control circuit determines from the sensed conditions a state of fibrillation.

12. The cardiac assist device as claimed in claim 1, wherein said lead system comprises a fiber optic based communication system.

13. The cardiac assist device as claimed in claim 1, wherein said lead system comprises a plurality of electrical leads.

14. The cardiac assist device as claimed in claim 13, wherein said plurality of electrical leads have a shielding therearound, said shielding preventing said electrical leads from conducting stray electromagnetic interference.

15. The cardiac assist device as claimed in claim 14, wherein said shielding is a metallic sheath to prevent said electrical leads from conducting stray electromagnetic interference.

16. The cardiac assist device as claimed in claim 14, wherein said shielding is a carbon composite sheath to prevent said electrical leads from conducting stray electromagnetic interference.

17. The cardiac assist device as claimed in claim 14, wherein said shielding is a polymer composite sheath to prevent said electrical leads from conducting stray electromagnetic interference.

18. The cardiac assist device as claimed in claim 13, wherein each electrical lead includes an electrical filter, said electrical filter removing stray electromagnetic interference from a signal being received from said electrical lead.

19. The cardiac assist device as claimed in claim 18, wherein said plurality of electrical leads have a shielding therearound, said shielding preventing said electrical leads from conducting stray electromagnetic interference.

20. The cardiac assist device as claimed in claim 19, wherein said shielding is a carbon composite sheath to prevent said electrical leads from conducting stray electromagnetic interference.

21. The cardiac assist device as claimed in claim 19, wherein said shielding is a polymer composite sheath to prevent said electrical leads from conducting stray electromagnetic interference.

22. A method for assisting a heart beat normally, comprising:
   (a) sensing conditions of a heart;
   (b) determining a state of the heart from the sensed conditions;
   (c) generating pre-fibrillation state electrical signal so as to bring a pre-fibrillated heart condition back into a normal beating condition when the determined state of the heart is a pre-state of fibrillation, and
   (d) generating an electrical enhancement signal, the electrical enhancement signal effectively lowering a threshold for pacing the heart when the determined state of the heart is a state associated with a natural pacing signal of the heart falling below a threshold to trigger the heart to beat.

23. The method as claimed in claim 22, wherein the electrical enhancement signal comprises a noise signal.

24. The method as claimed in claim 22, wherein the electrical enhancement signal comprises a periodic signal.

25. The method as claimed in claim 22, wherein the electrical enhancement signal comprises a high frequency deterministic signal.

26. The method as claimed in claim 22, wherein the electrical enhancement signal comprises a randomly fluctuating intensity signal.

27. The method as claimed in claim 22, wherein the electrical enhancement signal comprises a randomly fluctuating frequency signal.

28. The method as claimed in claim 22, wherein the electrical enhancement signal is modulated in response to the sensed subthreshold pacing signal.

29. The method as claimed in claim 22, wherein the conditions of the heart are sensed by measuring pressure waves upon a surface of the heart.

30. The method as claimed in claim 22, wherein the conditions of the heart are sensed by capacitively measuring a voltage waveform traveling across the heart.

31. The method as claimed in claim 22, further comprising:
   (e) generating a electrical pulse so as to defibrillate a fibrillated heart when the determined state of the heart is a state of fibrillation.

* * * * *